US00PP17839P2

(12) United States Plant Patent
Meyer

(10) Patent No.: US PP17,839 P2
(45) Date of Patent: Jun. 26, 2007

(54) ***IMPATIENS* PLANT NAMED 'BALCELBRISAL'**

(50) Latin Name: *Impatiens×hybrida*
Varietal Denomination: Balcelbrisal

(75) Inventor: Kerry M Meyer, St. Thomas, MO (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/296,834

(22) Filed: Dec. 7, 2005

(51) Int. Cl.
*A01H 5/00* (2006.01)

(52) U.S. Cl. ..... Plt./317

(58) Field of Classification Search ..... Plt./317
See application file for complete search history.

(56) References Cited

PUBLICATIONS

European Plant Breeders' Rights application No. 2005/2004 filed Oct. 25, 2005.

*Primary Examiner*—Anne Marie Grunberg
*Assistant Examiner*—S. B. McCormick-Ewoldt
(74) *Attorney, Agent, or Firm*—Audrey Charles

(57) ABSTRACT

A new and distinct cultivar of *Impatiens* plant named 'Balcelbrisal' characterized by its bright salmon-colored flowers, medium green-colored foliage, and vigorous, upright mounded growth habit.

1 Drawing Sheet

Latin name of genus and species of plant claimed: *Impatiens×hybrida.*
Variety denomination: 'Balcelbrisal'.

BACKGROUND OF THE INVENTION

The present invention relates to a new and distinct cultivar of *Impatiens* plant botanically known as *Impatiens×hybrida* and hereinafter referred to by the cultivar name 'Balcelbrisal'.

The new cultivar originated in a controlled breeding program in Arroyo Grande, Ca. during May 2002. The objective of the breeding program was the development of *Impatiens* cultivars with numerous large flowers, attractive flower colors, and freely basal branching growth habit.

The female (seed) parent of the new cultivar was the proprietary *Impatiens×hybrida* breeding selection designated BFP-2874, not patented, characterized by its medium pink-colored flowers, dark green-colored foliage, and compact, mounded growth habit. The male (pollen) parent of the new cultivar was 'Balcelneon', U.S. Plant Pat. No. 13,995, characterized by its red purple-colored flowers, each with a light pink-colored eye, that are positioned above and beyond the foliage, dark green-colored foliage, and upright, mounded and uniform plant habit. The new *Impatiens* was discovered and selected by the inventor as a single flowering plant within the progeny of the above stated cross-pollination during October 2002 in a controlled environment at Arroyo Grande, Calif.

Asexual reproduction of the new cultivar by terminal stem cuttings since October 2002 at Arroyo Grande, Calif. and West Chicago, Ill. has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balcelbrisal' as a new and distinct cultivar of *Impatiens* plant:

1. Bright salmon-colored flowers;
2. Medium green-colored foliage; and
3. Vigorous, upright mounded growth habit.

Plants of the new cultivar differ from plants of the female parent primarily in flower color and foliage color and from plants of the male parent primarily in flower color and foliage color.

Of the many commercially available *Impatiens* cultivars known to the inventor, the most similar in comparison to the new cultivar is the male parent 'Balcelneon', U.S. Plant Pat. No. 13,995. However, in side by side comparisons, plants of the new cultivar differ from plants of 'Balcelneon' in the following characteristics:

1. Plants of the new cultivar have a flower color different from plants of 'Balcelneon';
2. Plants of the new cultivar have a foliage color different from plants of 'Balcelneon';
3. Plants of the new cultivar have a branch color different from plants of 'Balcelneon'; and
4. Plants of the new cultivar have shorter peduncles than plants of 'Balcelneon'.

In addition, plants of the new cultivar can be compared to plants of 'Balcelsuna' U.S. Plant Pat. No. 14,000. Plants of the new cultivar differ from plants of 'Balcelsuna' in the following characteristics:

1. Plants of the new cultivar have a foliage color different from plants of 'Balcelsuna';
2. Plants of the new cultivar have a branch color different from plants of 'Balcelsuna'; and
3. Plants of the new cultivar have an upper surface petal color different from plants of 'Balcelsuna'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcelbrisal'. The plants were grown in 10 cm pots for 10 weeks in a greenhouse at West Chicago, Ill.

DETAILED BOTANICAL DESCRIPTION

Figure 1:
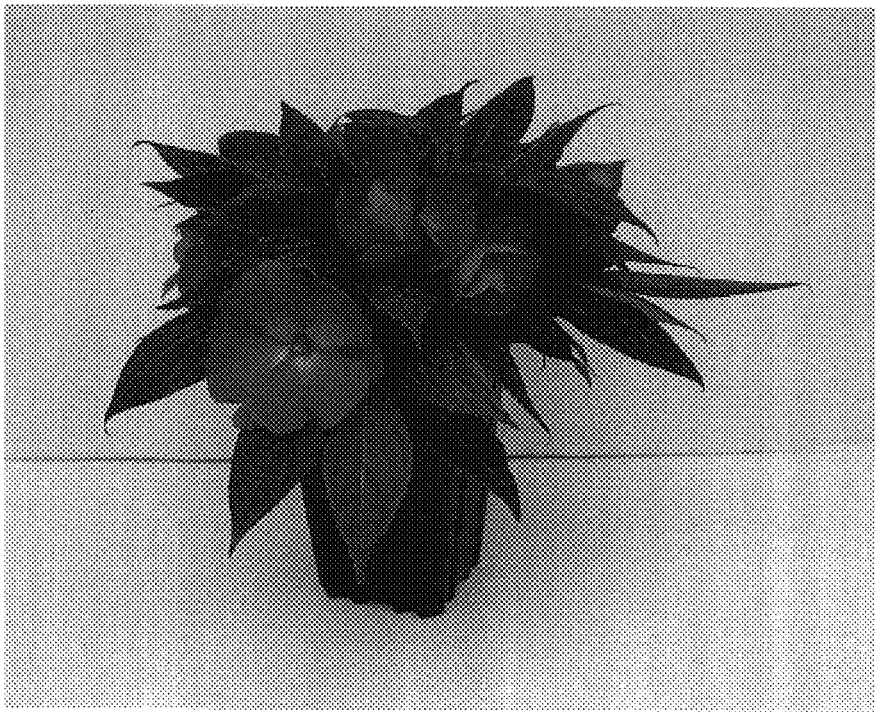
FIG. 1 illustrates a side view of the overall growth and flowering habit of 'Balcelbrisal'.
Figure 2:
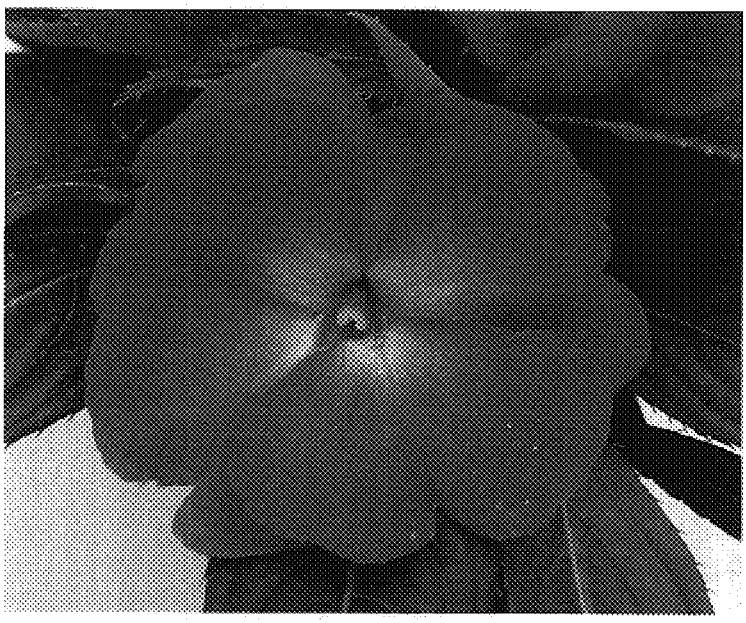
FIG. 2 illustrates a close-up view of an individual flower of 'Balcelbrisal'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The Royal Horticultural Society Colour Chart of The Royal Horticultural Society, London, England, 2001 edition, except where general color terms of ordinary significance are used. The color values were determined on Aug. 2, 2005 between 3:00 p.m. and 4:00 p.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 10 weeks utilizing a soilless growth medium. Greenhouse temperatures were maintained at approximately 68° F. to 75° F. (20° C. to 24° C.) during the day and approximately 58° F. to 65° F. (14° C. to 18° C.) during the night. Greenhouse light levels of 4,000 to 7,000 footcandles were maintained during the day.

Botanical classification: *Impatiens×hybrida* cultivar Balcelbrisal.

Parentage:

*Female parent.*—Proprietary *Impatiens×hybrida* breeding selection designated BFP-2874, not patented.

*Male parent.*—'Balcelneon', U.S. Plant Pat. No. 13,995.

Propagation:

*Type cutting.*—Terminal stem.

*Time to initiate roots.*—Approximately 7 to 8 days.

*Time to produce a rooted cutting.*—Approximately 21 to 28 days.

*Root description.*—Fine and fibrous.

*Rooting habit.*—Freely branching.

Plant description:

*Crop time.*—Approximately 7 to 9 weeks from a rooted cutting.

*Growth habit and general appearance.*—Vigorous, upright, mounded.

*Size.*—Height from soil level to top of plant plane: Approximately 15.3 cm. Width: Approximately 44.9 cm.

*Branching habit.*—Freely basal branching. Approximately 5 branches per plant.

*Branch.*—Strength: Strong. Length: Approximately 8.7 cm. Diameter: Approximately 9.3 mm. Texture: Glabrous. Color: 144B with overlay of 187A especially at node regions. Internode length at center of branch: Approximately 2.2 cm.

*Foliage.*—Number of leaves per main branch: Approximately 13. Fragrance: None. Form: Simple. Arrangement: In whorls of 3 to 5. Aspect: Petiole is at an acute angle to stem and leaf blade is perpendicular to stem. Shape: Elliptic. Margin: Serrate, ciliate. Apex: Acuminate. Base: Attenuate. Venation pattern: Pinnate. Length of leaf at center of stem: Approximately 12.1 cm. Width of leaf at center of stem: Approximately 4.0 cm. Texture of upper surface: Glabrous. Texture of lower surface: Glabrous with puberulent midvein. Color of upper surface of mature foliage: Darker than 137A with venation of 144C. Color of lower surface of mature foliage: Closest to 138A with venation of 137C. Petiole length: Approximately 1.9 cm. Petiole diameter: Approximately 3.4 mm. Petiole texture: Glabrous: Petiole color: 144C with overlay of 178A.

Flowering description:

*Flowering habit.*—'Balcelbrisal' is freely flowering under outdoor growing conditions with substantially continuous blooming from spring through autumn and year round in greenhouse environment.

*Time to first flower.*—Approximately 12 weeks from sticking of unrooted cutting.

*Lastingness of individual bloom.*—Approximately 5 to 7 days.

Flower description:

*Type.*—Single. Quantity per plant at ten weeks: Approximately 6. Fragrance: None.

*Bud rate of opening.*—Generally takes 4 to 6 days for bud to progress from first color to fully open flower.

*Bud just before opening.*—Shape: Oval. Quantity showing color: Approximately 13 at 10 weeks. Length: Approximately 1.4 cm. Diameter: Approximately 9.1 mm. Color: 52A.

*Corolla.*—Shape: Round, cupped when first open petals turn downward with age. Diameter: Approximately 7.6 cm. Depth: Approximately 1.9 cm. Borne: Above and below foliage.

*Petals.*—Quantity: 5. Shape: Obovate. Aspect: Flat. Appearance: Iridescent. Margin: Entire. Apex: Emarginate. Texture: Glabrous. Base of upper petal: Truncate. Base of lateral and lower petals: Attenuate. Length of upper petal: Approximately 3.2 cm. Width of upper petal: Approximately 5.0 cm. Length of lateral petals: Approximately 3.7 cm. Width of lateral petals: Approximately 4.1 cm. Length of lower petal: Approximately 4.3 cm. Width of lower petal: Approximately 4.3 cm. Color of upper surface of all petals when fully open: Darker than 52A with area at base of N74D and 64B at attachment point. Color of lower surface of all petals when fully open: 52A with 68A at attachment point.

*Spur.*—Quantity: One per flower. Length: Approximately 5.4 cm. Diameter at tip: Approximately 2.9 mm. Diameter at base: Approximately 0.8 mm. Texture: Glabrous. Color: N155C at base gradually darkening to 60A near apex with tip of 144C.

*Peduncle.*—Strength: Strong. Aspect: Acute angle to stem. Length: Approximately 5.0 cm. Diameter: Approximately 1.4 mm. Texture: Glabrous. Color: 144B with overlay of 178A.

*Calyx.*—Quantity of sepals per flower: 4 with one fused to base of upper petal. Apex: Acuminate. Texture of upper and lower surfaces: Glabrous. Shape of lateral sepal: Ovate. Length of lateral sepal: Approximately 1.5 cm. Width of lateral sepal: Approximately 5.4 mm. Color of lateral sepal: N144D. Shape of lower sepal: Ovate. Length of lower sepal: Approximately 1.9 cm. Width of lower sepal: Approximately 1.5 cm. Color of lower sepal: N155C in center with 63C at margins and N144C at tip.

*Reproductive organs.*—Androecium: Stamen quantity: 5. Anther shape: Hooded. Anther length: Approximately 3.0 mm. Anther color: 7D. Pollen amount: Abundant. Pollen color: 11D. Gynoecium: Pistil quantity: One per flower. Pistil length: Approximately 5.2 mm. Stigma shape: Five pointed star. Stigma length: Approximately 0.2 mm. Stigma color: Colorless, transparent. Style length: Approximately 1.0 mm. Style color: 150D. Ovary length: Approximately 4.0 mm. Ovary diameter: Approximately 2.0 mm. Ovary texture: Glabrous. Ovary color: Closest to 143C.

Seed and fruit production: Neither seed nor fruit production has been observed.

Disease and pest resistance: Resistance to pathogens and pests common to *Impatiens* has not been observed.

What is claimed is:

1. A new and distinct cultivar of *Impatiens* plant named 'Balcelbrisal', substantially as herein shown and described.

* * * * *